(12) United States Patent
Thompson et al.

(10) Patent No.: US 12,029,498 B2
(45) Date of Patent: *Jul. 9, 2024

(54) OPTICAL-FIBER CONNECTOR MODULES INCLUDING SHAPE-SENSING SYSTEMS AND METHODS THEREOF

(71) Applicant: Bard Access Systems, Inc., Salt Lake City, UT (US)

(72) Inventors: Chase Thompson, Bountiful, UT (US); Anthony K. Misener, Bountiful, UT (US); Shayne Messerly, Kaysville, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 619 days.

This patent is subject to a terminal disclaimer.

(21) Appl. No.: 16/988,452

(22) Filed: Aug. 7, 2020

(65) Prior Publication Data

US 2021/0038322 A1 Feb. 11, 2021

Related U.S. Application Data

(60) Provisional application No. 62/884,602, filed on Aug. 8, 2019.

(51) Int. Cl.
*A61B 34/20* (2016.01)
*G02B 6/02* (2006.01)

(52) U.S. Cl.
CPC .......... *A61B 34/20* (2016.02); *G02B 6/02076* (2013.01); *A61B 2034/2061* (2016.02)

(58) Field of Classification Search
CPC ............ A61B 2034/2061; A61B 34/20; A61B 1/00126
See application file for complete search history.

(56) References Cited

U.S. PATENT DOCUMENTS 2,831,174 A 4/1958 Hilmo
2,959,766 A 11/1960 Edwin
(Continued)

FOREIGN PATENT DOCUMENTS

EP 1318576 A1 6/2003
EP 3270817 A1 1/2018
(Continued)

OTHER PUBLICATIONS

PCT/US2019/018851 filed Feb. 20, 2019 International Preliminary Report on Patentability dated May 7, 2019.
(Continued)

*Primary Examiner* — Amelie R Davis
(74) *Attorney, Agent, or Firm* — Rutan & Tucker LLP (57) ABSTRACT

Optical-fiber connector modules are disclosed. In one example, an optical-fiber connector module can include a receptacle disposed in a housing, a cable extending from the housing, and an optical fiber within at least the cable. The receptacle can be configured to accept insertion of a first plug for establishing a first optical connection between the optical-fiber connector module and an optical-fiber stylet of a medical device. The cable can include a second plug for establishing a second optical connection between the optical-fiber connector module and an optical interrogator. The optical fiber extends from the receptacle through the cable to the second plug. The optical fiber can be configured to convey input optical signals from the optical interrogator to the optical-fiber stylet and reflected optical signals from the optical-fiber stylet to the optical interrogator. Shape-sensing systems including the optical-fiber connector modules and methods of the foregoing are also disclosed.

16 Claims, 7 Drawing Sheets

(56) References Cited

U.S. PATENT DOCUMENTS

| | | |
|---|---|---|
| 3,329,928 A | 7/1967 | Broske |
| 3,532,095 A | 10/1970 | Miller et al. |
| 3,597,582 A | 8/1971 | Goode et al. |
| 3,605,743 A | 9/1971 | Arce |
| 3,649,952 A | 3/1972 | Harmon |
| 3,665,372 A | 5/1972 | Goode et al. |
| 3,673,548 A | 6/1972 | Mattingly, Jr. et al. |
| 3,746,814 A | 7/1973 | Ackey et al. |
| 3,824,556 A | 7/1974 | Berkovits et al. |
| 3,842,394 A | 10/1974 | Bolduc |
| 4,200,348 A | 4/1980 | Stupay |
| 4,220,387 A | 9/1980 | Biche et al. |
| 4,254,764 A | 3/1981 | Neward |
| 4,303,293 A | 12/1981 | Grunwald |
| 4,369,794 A | 1/1983 | Furler |
| 4,490,003 A | 12/1984 | Robinson |
| 4,614,395 A | 9/1986 | Peers-Trevarton |
| 4,632,121 A | 12/1986 | Johnson et al. |
| 4,700,997 A | 10/1987 | Strand |
| 4,702,256 A | 10/1987 | Robinson et al. |
| 4,761,143 A | 8/1988 | Owens et al. |
| 4,858,810 A | 8/1989 | Intlekofer et al. |
| 4,860,742 A | 8/1989 | Park et al. |
| 4,973,329 A | 11/1990 | Park et al. |
| 5,159,861 A | 11/1992 | Anderson |
| 5,178,159 A | 1/1993 | Christian |
| 5,217,435 A | 6/1993 | Kring |
| 5,325,746 A | 7/1994 | Anderson |
| 5,325,868 A | 7/1994 | Kimmelstiel |
| 5,334,045 A | 8/1994 | Cappa et al. |
| 5,354,326 A | 10/1994 | Comben et al. |
| 5,407,368 A | 4/1995 | Strand et al. |
| 5,423,877 A | 6/1995 | Mackey |
| 5,437,277 A | 8/1995 | Dumoulin et al. |
| 5,454,739 A | 10/1995 | Strand |
| 5,482,038 A | 1/1996 | Ruff |
| 5,489,225 A | 2/1996 | Julian |
| 5,501,675 A | 3/1996 | Erskine |
| 5,538,444 A | 7/1996 | Strand et al. |
| 5,560,358 A | 10/1996 | Arnold et al. |
| 5,591,119 A | 1/1997 | Adair |
| 5,624,281 A | 4/1997 | Christensson |
| 5,685,855 A | 11/1997 | Erskine |
| 5,752,915 A | 5/1998 | Neubauer et al. |
| 5,766,042 A | 6/1998 | Ries et al. |
| 5,769,786 A | 6/1998 | Wiegel |
| 5,797,880 A | 8/1998 | Erskine |
| 5,840,024 A | 11/1998 | Taniguchi et al. |
| 5,968,082 A | 10/1999 | Heil |
| 5,984,918 A | 11/1999 | Garito et al. |
| 6,050,976 A | 4/2000 | Thorne et al. |
| 6,090,052 A | 7/2000 | Akerfeldt et al. |
| 6,102,044 A | 8/2000 | Naidyhorski |
| 6,132,368 A | 10/2000 | Cooper |
| 6,140,722 A | 10/2000 | Ballard et al. |
| 6,162,101 A | 12/2000 | Fischer et al. |
| 6,319,015 B1 | 11/2001 | Faunce |
| 6,324,416 B1 | 11/2001 | Seibert |
| 6,330,480 B1 | 12/2001 | Van der Linden et al. |
| 6,350,160 B1 | 2/2002 | Feuersanger et al. |
| 6,415,168 B1 | 7/2002 | Putz |
| 6,428,336 B1 | 8/2002 | Akerfeldt |
| 6,546,270 B1 | 4/2003 | Goldin et al. |
| 6,620,136 B1 | 9/2003 | Pressly, Sr. et al. |
| 6,663,570 B2 | 12/2003 | Mott et al. |
| 6,673,078 B1 | 1/2004 | Muncie |
| 6,714,809 B2 | 3/2004 | Lee et al. |
| 6,780,065 B2 | 8/2004 | Schwarz |
| 6,799,991 B2 | 10/2004 | Williams et al. |
| 6,913,478 B2 | 7/2005 | Lamirey |
| 7,130,699 B2 | 10/2006 | Huff et al. |
| 7,144,378 B2 | 12/2006 | Arnott |
| 7,255,609 B1 | 8/2007 | Epstein |
| 7,274,956 B2 | 9/2007 | Mott et al. |
| 7,402,083 B2 | 7/2008 | Kast et al. |
| 7,452,360 B2 | 11/2008 | Trudeau et al. |
| 7,553,193 B2 | 6/2009 | Kast et al. |
| 7,585,118 B1 | 9/2009 | Lumpkin |
| 7,633,023 B1 | 12/2009 | Cappa et al. |
| 7,666,191 B2 | 2/2010 | Orban, III et al. |
| 7,753,696 B2 | 7/2010 | Hoecke et al. |
| 7,771,394 B2 | 8/2010 | Shue et al. |
| 7,819,844 B2 | 10/2010 | Spenser et al. |
| 7,972,282 B2 | 7/2011 | Clark et al. |
| 8,105,338 B2 | 1/2012 | Anderson et al. |
| 8,147,275 B1 | 4/2012 | Drake et al. |
| 8,206,175 B2 | 6/2012 | Boyd et al. |
| 8,267,873 B2 | 9/2012 | Yanuma |
| 8,388,541 B2 | 3/2013 | Messerly et al. |
| 8,480,427 B2 | 7/2013 | Marshalok |
| 8,548,601 B2 | 10/2013 | Chinn et al. |
| 8,597,042 B2 | 12/2013 | King |
| 8,603,011 B2 | 12/2013 | Landowski |
| 8,620,412 B2 | 12/2013 | Griffiths et al. |
| 8,639,340 B2 | 1/2014 | Sommer et al. |
| 8,666,510 B2 | 3/2014 | Chinn et al. |
| 8,781,555 B2 | 7/2014 | Burnside et al. |
| 8,849,382 B2 | 9/2014 | Cox et al. |
| 8,869,887 B2 | 10/2014 | Deere et al. |
| 8,932,258 B2 | 1/2015 | Blanchard et al. |
| 8,958,878 B2 | 2/2015 | Cejnar |
| 9,059,548 B2 | 6/2015 | Stump et al. |
| 9,095,680 B2 | 8/2015 | Steegers et al. |
| 9,101,775 B2 | 8/2015 | Barker |
| 9,107,594 B2 | 8/2015 | Selvitelli et al. |
| 9,108,027 B2 | 8/2015 | Eubanks et al. |
| 9,131,956 B2 | 9/2015 | Shaughnessy et al. |
| 9,144,395 B2 | 9/2015 | Sela et al. |
| 9,425,537 B2 | 8/2016 | Barker |
| 9,456,766 B2 | 10/2016 | Cox et al. |
| 9,492,097 B2 | 11/2016 | Wilkes et al. |
| 9,521,961 B2 | 12/2016 | Silverstein et al. |
| 9,526,440 B2 | 12/2016 | Burnside et al. |
| 9,549,685 B2 | 1/2017 | Cox et al. |
| 9,554,716 B2 | 1/2017 | Burnside et al. |
| 9,636,031 B2 | 5/2017 | Cox |
| 9,649,048 B2 | 5/2017 | Cox et al. |
| 9,656,093 B2 | 5/2017 | Villarta et al. |
| 9,662,506 B2 | 5/2017 | Govea |
| 9,675,784 B2 | 6/2017 | Belson |
| 9,681,823 B2 | 6/2017 | Messerly et al. |
| 9,808,647 B2 | 11/2017 | Rhodes et al. |
| 9,872,971 B2 | 1/2018 | Blanchard |
| 9,919,145 B2 | 3/2018 | Bondhus et al. |
| 9,950,139 B2 | 4/2018 | Blanchard et al. |
| 9,999,371 B2 | 6/2018 | Messerly et al. |
| 10,105,121 B2 | 10/2018 | Burnside et al. |
| 10,130,806 B2 | 11/2018 | Leven et al. |
| 10,165,962 B2 | 1/2019 | Messerly et al. |
| 10,201,713 B2 | 2/2019 | Leven |
| 10,231,753 B2 | 3/2019 | Burnside et al. |
| 10,238,418 B2 | 3/2019 | Cox et al. |
| 10,238,880 B2 | 3/2019 | Thom et al. |
| 10,307,602 B2 | 6/2019 | Leven |
| 10,322,253 B2 | 6/2019 | Einav et al. |
| 10,342,575 B2 | 7/2019 | Cox et al. |
| 10,449,330 B2 | 10/2019 | Newman et al. |
| 10,524,691 B2 | 1/2020 | Newman et al. |
| 10,602,958 B2 | 3/2020 | Silverstein et al. |
| 10,751,509 B2 | 8/2020 | Misener |
| 10,772,696 B2 | 9/2020 | Thompson et al. |
| 10,992,078 B2 | 4/2021 | Thompson et al. |
| D921,884 S | 6/2021 | Tran et al. |
| 2002/0197905 A1 | 12/2002 | Kaufmann et al. |
| 2003/0199827 A1 | 10/2003 | Thorne |
| 2003/0216723 A1 | 11/2003 | Shinmura et al. |
| 2004/0039372 A1 | 2/2004 | Carmody |
| 2004/0146252 A1 | 7/2004 | Healy et al. |
| 2005/0177199 A1 | 8/2005 | Hansen et al. |
| 2005/0283216 A1 | 12/2005 | Pyles |
| 2006/0025677 A1 | 2/2006 | Verard et al. |
| 2006/0030864 A1 | 2/2006 | Kennedy et al. |
| 2006/0161138 A1 | 7/2006 | Orban et al. |
| 2006/0173407 A1 | 8/2006 | Shaughnessy et al. |

(56) References Cited

U.S. PATENT DOCUMENTS

| | | |
|---|---|---|
| 2007/0062544 A1 | 3/2007 | Rauk Bergstrom et al. |
| 2007/0118079 A1 | 5/2007 | Moberg et al. |
| 2007/0160327 A1 | 7/2007 | Lewallen et al. |
| 2007/0161969 A1 | 7/2007 | Andersen |
| 2007/0293719 A1 | 12/2007 | Scopton et al. |
| 2008/0009720 A1 | 1/2008 | Schefelker et al. |
| 2008/0046062 A1 | 2/2008 | Camps et al. |
| 2008/0236598 A1 | 10/2008 | Gobel |
| 2008/0287876 A1 | 11/2008 | Shue et al. |
| 2008/0304793 A1 | 12/2008 | Benaron et al. |
| 2009/0156926 A1 | 6/2009 | Messerly et al. |
| 2009/0234328 A1 | 9/2009 | Cox et al. |
| 2010/0036227 A1 | 2/2010 | Cox et al. |
| 2010/0049126 A1 | 2/2010 | Bronfeld et al. |
| 2010/0139669 A1 | 6/2010 | Piferi et al. |
| 2010/0204569 A1 | 8/2010 | Burnside et al. |
| 2011/0000155 A1 | 1/2011 | Cox et al. |
| 2011/0160824 A1 | 6/2011 | Ware et al. |
| 2011/0166528 A1 | 7/2011 | Millerd et al. |
| 2011/0250775 A1 | 10/2011 | Bies et al. |
| 2011/0257503 A1 | 10/2011 | Mehdizadeh et al. |
| 2011/0002821 A1 | 11/2011 | Burnside et al. |
| 2011/0002951 A1 | 12/2011 | Cox et al. |
| 2012/0071752 A1 | 3/2012 | Sewell et al. |
| 2012/0001430 A1 | 6/2012 | Silverstein et al. |
| 2012/0002208 A1 | 8/2012 | Messerly et al. |
| 2012/0253320 A1 | 10/2012 | Steegers et al. |
| 2013/0000061 A1 | 1/2013 | Wilkes et al. |
| 2013/0023729 A1 | 1/2013 | Vazales et al. |
| 2013/0000601 A1 | 3/2013 | Messerly et al. |
| 2013/0095689 A1 | 4/2013 | Hayman et al. |
| 2013/0104884 A1 | 5/2013 | Vazales et al. |
| 2013/0109980 A1 | 5/2013 | Teo |
| 2013/0211225 A1 | 8/2013 | Zhang |
| 2013/0002454 A1 | 9/2013 | Messerly et al. |
| 2013/0247921 A1 | 9/2013 | Dye et al. |
| 2013/0289417 A1 | 10/2013 | Grunwald et al. |
| 2013/0308137 A1 | 11/2013 | Manzke et al. |
| 2013/0331688 A1 | 12/2013 | Heigl et al. |
| 2013/0337674 A1 | 12/2013 | Stump et al. |
| 2014/0000316 A1 | 1/2014 | Newman et al. |
| 2014/0000462 A1 | 2/2014 | Newman et al. |
| 2014/0001074 A1 | 4/2014 | Cox et al. |
| 2014/0150782 A1 | 6/2014 | Vazales et al. |
| 2014/0001881 A1 | 7/2014 | Misener |
| 2014/0003034 A1 | 10/2014 | Burnside et al. |
| 2015/0000187 A1 | 1/2015 | Cox et al. |
| 2015/0012072 A1 | 1/2015 | Johnson et al. |
| 2015/0031987 A1 | 1/2015 | Pameijer et al. |
| 2015/0105654 A1 | 4/2015 | Meyer |
| 2015/0148615 A1 | 5/2015 | Brennan et al. |
| 2015/0164583 A1 | 6/2015 | Zarins et al. |
| 2015/0177467 A1 | 6/2015 | Gniadek et al. |
| 2015/0190615 A1 | 7/2015 | Shaltis |
| 2015/0223897 A1 | 8/2015 | Kostrzewski et al. |
| 2015/0002971 A1 | 10/2015 | Cox et al. |
| 2015/0305816 A1 | 10/2015 | Hadzic |
| 2016/0018602 A1 | 1/2016 | Govari et al. |
| 2016/0213432 A1* | 7/2016 | Flexman ............... A61B 5/065 |
| 2017/0000205 A1 | 1/2017 | Cox et al. |
| 2017/0014194 A1* | 1/2017 | Duindam .......... A61B 17/3209 |
| 2017/0000795 A1 | 3/2017 | Silverstein et al. |
| 2017/0000796 A1 | 3/2017 | Burnside et al. |
| 2017/0181646 A1* | 6/2017 | Hayes .................. A61B 5/1459 |
| 2017/0231700 A1 | 8/2017 | Cox et al. |
| 2017/0261699 A1 | 9/2017 | Compton et al. |
| 2017/0002810 A1 | 10/2017 | Messerly et al. |
| 2017/0333136 A1 | 11/2017 | Hladio et al. |
| 2018/0071509 A1 | 3/2018 | Tran et al. |
| 2018/0110951 A2 | 4/2018 | Beard |
| 2018/0001165 A1 | 5/2018 | Newman et al. |
| 2018/0140170 A1 | 5/2018 | Van Putten et al. |
| 2018/0002961 A1 | 10/2018 | Messerly et al. |
| 2018/0289927 A1 | 10/2018 | Messerly |
| 2019/0000698 A1 | 3/2019 | Burnside et al. |
| 2019/0069877 A1 | 3/2019 | Burnside et al. |
| 2019/0000991 A1 | 4/2019 | Messerly et al. |
| 2019/0180647 A1* | 6/2019 | Fujiki ...................... H04R 1/02 |
| 2019/0231172 A1 | 8/2019 | Barron et al. |
| 2019/0237902 A1 | 8/2019 | Thompson et al. |
| 2019/0350621 A1 | 11/2019 | Zitnick et al. |
| 2019/0350663 A1 | 11/2019 | Thompson et al. |
| 2020/0000548 A1 | 2/2020 | Newman et al. |
| 2020/0001383 A1 | 5/2020 | Newman et al. |
| 2020/0002372 A1 | 7/2020 | Silverstein et al. |
| 2020/0221934 A1* | 7/2020 | Van Der Mark .. A61B 1/00128 |
| 2020/0345441 A1 | 11/2020 | Thompson et al. |
| 2021/0030504 A1 | 2/2021 | Thompson et al. |
| 2022/0110707 A1 | 4/2022 | Sowards et al. |
| 2022/0110708 A1 | 4/2022 | Misener et al. |
| 2022/0128770 A1 | 4/2022 | Sowards et al. |
| 2022/0241044 A1 | 8/2022 | Thompson et al. |
| 2023/0248459 A1 | 8/2023 | Thompson et al. |

FOREIGN PATENT DOCUMENTS

| | | |
|---|---|---|
| EP | 3673801 A1 | 7/2020 |
| WO | 9413201 A1 | 6/1994 |
| WO | 9619017 A1 | 6/1996 |
| WO | 9822180 A1 | 5/1998 |
| WO | 2004101068 A1 | 11/2004 |
| WO | 2005016451 A1 | 2/2005 |
| WO | 2005044332 A2 | 5/2005 |
| WO | 2005072807 A1 | 8/2005 |
| WO | 2005077453 A2 | 8/2005 |
| WO | 2007058816 A2 | 5/2007 |
| WO | 2007109285 A2 | 9/2007 |
| WO | 2007149618 A2 | 12/2007 |
| WO | 2009050599 A2 | 4/2009 |
| WO | 2010123701 A1 | 10/2010 |
| WO | 2011033107 A1 | 3/2011 |
| WO | 2011082160 A2 | 7/2011 |
| WO | 2012102745 A2 | 8/2012 |
| WO | 2015075002 A1 | 5/2015 |
| WO | 2016/146993 A1 | 9/2016 |
| WO | 2019/148201 A1 | 8/2019 |
| WO | 2019/165011 A1 | 8/2019 |
| WO | 2019/221926 A1 | 11/2019 |
| WO | 2021021408 A1 | 2/2021 |
| WO | 2021026502 A1 | 2/2021 |
| WO | 2022/081583 A1 | 4/2022 |
| WO | 2022081591 A1 | 4/2022 |
| WO | 2022/093991 A1 | 5/2022 |

OTHER PUBLICATIONS

PCT/US2020/41267 filed Jul. 8, 2020 Internation Search Report and Written Opinion dated Oct. 1, 2020.

PCT/US2020/45498 filed Aug. 7, 2020 International Search Report and Written Opinion dated Oct. 4, 2020.

U.S. Appl. No. 16/261,368, filed Jan. 29, 2019 Notice of Allowance dated Jan. 15, 2021.

U.S. Appl. No. 17/512,501, filed Oct. 27, 2021 Restriction Requirement dated Sep. 30, 2022.

U.S. Appl. No. 17/723,246, filed Apr. 18, 2022, Non-Final Office Action dated Sep. 27, 2022.

PCT/US2019/015710 filed Jan. 29, 2019 International Preliminary Report on Patentability dated Aug. 13, 2020.

PCT/US2019/015710 filed Jan. 29, 2019 International Search Report and Written Opinion dated Apr. 29, 2019.

PCT/US2019/018851 filed Feb. 20, 2019 Internation Search Report and Written Opinion dated May 7, 2019.

U.S. Appl. No. 12/426,175, filed Apr. 17, 2009 Advisory Action dated Nov. 26, 2013.

U.S. Appl. No. 12/426,175, filed Apr. 17, 2009 Decision on Appeal dated Nov. 7, 2016.

U.S. Appl. No. 12/426,175, filed Apr. 17, 2009 Examiner's Answer dated Oct. 7, 2014.

U.S. Appl. No. 12/426,175, filed Apr. 17, 2009 Final Office Action dated Aug. 2, 2013.

(56) References Cited

OTHER PUBLICATIONS

U.S. Appl. No. 12/426,175, filed Apr. 17, 2009 Final Office Action dated Jan. 31, 2014.
U.S. Appl. No. 12/426,175, filed Apr. 17, 2009 Non-Final Office Action dated Dec. 3, 2012.
U.S. Appl. No. 12/426,175, filed Apr. 17, 2009 Notice of Allowance dated Dec. 13, 2016.
U.S. Appl. No. 12/715,556, filed Mar. 2, 2010 Final Office Action dated Oct. 2, 2013.
U.S. Appl. No. 12/715,556, filed Mar. 2, 2010 Non-Final Office Action dated Sep. 13, 2012.
U.S. Appl. No. 15/585,051, filed May 2, 2017 Examiner's Answer dated May 2, 2019.
U.S. Appl. No. 15/585,051, filed May 2, 2017 Final Office Action dated Feb. 28, 2018.
U.S. Appl. No. 15/585,051, filed May 2, 2017 Final Office Action dated Mar. 15, 2018.
U.S. Appl. No. 15/585,051, filed May 2, 2017 Non-Final Office Action dated Jul. 14, 2017.
U.S. Appl. No. 16/261,368, filed Jan. 29, 2019 Advisory Action dated Jul. 21, 2020.
U.S. Appl. No. 16/261,368, filed Jan. 29, 2019 Non-Final Office Action dated Jan. 23, 2020.
U.S. Appl. No. 16/281,079, filed Feb. 20, 2019 Final Office Action dated Aug. 25, 2020.
U.S. Appl. No. 16/281,079, filed Feb. 20, 2019 Non-Final Office Action dated Apr. 1, 2020.
U.S. Appl. No. 16/402,074, filed May 2, 2019 Non-Final Office Action dated Apr. 16, 2020.
Design U.S. Appl. No. 29/658,136 Specification and Drawings filed Jul. 27, 2018.
"Sampling Accessories" Spectrometers Accessories Catalogue, pp. 71-102, XP055014465, retrieved from the Internet URL: http//www.mikropack.de/d/specto/pdfy-downoads/sampling accessories. pdf, Jan. 1, 2004 (Jan. 1, 2004).
PCT/US2021/054593 filed Oct. 12, 2021 International Search Report and Written Opinion dated Jan. 24, 2022.
PCT/US2021/056896 filed Oct. 27, 2021 International Search Report and Written Opinion dated Mar. 22, 2022.
U.S. Appl. No. 16/281,079, filed Feb. 20, 2019 Examiner's Answer dated Feb. 25, 2022.
PCT/US2021/054607 filed Oct. 12, 2021 Internation Search Report and Written Opinion dated Jan. 21, 2022.
U.S. Appl. No. 16/281,079, filed Feb. 20, 2019 Non-Final Office Action dated Apr. 20, 2021.
U.S. Appl. No. 16/932,425, filed Jul. 17, 2020 Non-Final Office Action dated Jun. 18, 2021.
U.S. Appl. No. 16/932,425, filed Jul. 17, 2020 Notice of Allowance dated Jan. 10, 2022.
PCT/US19/30470 filed May 2, 2019 International Search Report and Written Opinion dated Jul. 19, 2019.
U.S. Appl. No. 16/923,912, filed Jul. 8, 2020 Notice of Allowance dated Mar. 27, 2023.
U.S. Appl. No. 17/512,501, filed Oct. 27, 2021 Non-Final Office Action dated Feb. 17, 2023.
U.S. Appl. No. 17/723,246, filed Apr. 18, 2022, Notice of Allowance dated Jan. 27, 2023.
EP 20849119.1 filed Mar. 4, 2022 Extended European Search Report dated Jun. 26, 2023.
U.S. Appl. No. 16/281,079, filed Feb. 20, 2019 Board Decision dated Jun. 6, 2023.
U.S. Appl. No. 17/240,826, filed Apr. 26, 2021, Non-Final Office Action dated Jul. 19, 2023.
U.S. Appl. No. 18/235,334, filed Aug. 17, 2023, Notice of Allowance dated Apr. 4, 2024.

\* cited by examiner

OPTICAL-FIBER CONNECTOR MODULES INCLUDING SHAPE-SENSING SYSTEMS AND METHODS THEREOF

PRIORITY

This application claims the benefit of priority to U.S. Provisional Application No. 62/884,602, filed Aug. 8, 2019, which is incorporated by reference in its entirety into this application.

BACKGROUND

At times, a tip of a peripherally inserted central catheter ("PICC") or central venous catheter ("CVC") can move becoming displaced from an ideal position in a patient's superior vena cava ("SVC"). A clinician believing such a PICC or CVC has displaced typically checks for displacement by chest X-ray and replaces the PICC or CVC if necessary. Because X-rays expose patients to ionizing radiation, medical devices such as PICCs and CVCs are being developed with integrated optical-fiber stylets for clinicians to easily and safely check for displacement thereof. However, in order for the clinicians to check for displacement, the PICCs or CVCs, which are sterile as provided, need to be at least optically connected to non-sterile capital equipment without compromising sterile conditions. Therefore, there is a need for an optical-fiber connector module that allows for single-use medical devices such as the foregoing PICCs and CVCs to be at least optically connected to non-sterile capital equipment without compromising sterile conditions.

Disclosed herein are optical-fiber connector modules, shape-sensing systems including the optical-fiber connector modules, and methods thereof.

SUMMARY

Disclosed herein is an optical-fiber connector module including, in some embodiments, a housing, a receptacle disposed in the housing, a cable extending from the housing, and an optical fiber within at least the cable. The receptacle is configured to accept insertion of a first plug for establishing a first optical connection between the optical-fiber connector module and an optical-fiber stylet of a medical device. The cable includes a second plug for establishing a second optical connection between the optical-fiber connector module and an optical interrogator. The optical fiber extends from the receptacle through the cable to the second plug. The optical fiber is configured to convey input optical signals from the optical interrogator to the optical-fiber stylet and reflected optical signals from the optical-fiber stylet to the optical interrogator.

In some embodiments, the optical-fiber connector module further includes one or more sensors selected from a gyroscope, an accelerometer, and a magnetometer disposed within the housing. The one or more sensors are configured to provide sensor data for determining a reference plane for shape sensing with the optical-fiber stylet.

In some embodiments, the optical-fiber connector module further includes power and data wires extending from the one or more sensors through the cable to the second plug or a third plug. The power and data wires are configured to respectively convey power to the one or more sensors and data from the one or more sensors.

In some embodiments, the optical-fiber connection module is configured to sit within a fenestration of a surgical drape adjacent a percutaneous insertion site for a catheter.

In some embodiments, the optical-fiber connection module is amenable to high-level disinfection or sterilization.

In some embodiments, the optical-fiber connection module is configured to sit beneath a surgical drape on a patient's chest.

In some embodiments, the housing includes a loop extending from the housing, a tether point integrated into the housing, or a ball-lock-pin receiver integrated into the housing configured for attaching a neck strap to the optical-fiber connector module. The loop, the tether point, or the ball-lock-pin receiver enables the optical-fiber connector module to be secured to the patient's neck while sitting on the patient's chest.

In some embodiments, the housing includes a patient-facing surface configured to be adhered to the patient's chest. The patient-facing surface enables the optical-fiber connector module to be secured to the patient's chest while sitting on the patient's chest.

In some embodiments, the receptacle includes an optical receiver configured to accept insertion of an optical terminal of the first plug and form an optical connection when the first plug is inserted into the receptacle with the surgical drape therebetween. The receptacle and the first plug enable at least the optical connection from a sterile field to a non-sterile field.

Also disclosed herein is a shape-sensing system for medical devices including, in some embodiments, a medical device, a console, and optical-fiber connector module configured for connecting the medical device to the console. The medical device includes an integrated optical-fiber stylet having a number of fiber Bragg grating ("FBG") sensors along a length of the optical-fiber stylet. The console includes memory and one or more processors for converting reflected optical signals from the optical-fiber stylet into shapes for the medical device for display. The optical-fiber connector module includes a receptacle disposed in a housing, a cable extending from the housing, and an optical fiber within at least the cable. The receptacle is configured to accept insertion of a first plug of the medical device for establishing a first optical connection between the optical-fiber connector module and the optical-fiber stylet. The cable includes a second plug for establishing a second optical connection between the optical-fiber connector module and an optical interrogator. The optical fiber extends from the receptacle through the cable to the second plug. The optical fiber is configured to convey input optical signals from the optical interrogator to the optical-fiber stylet and the reflected optical signals from the optical-fiber stylet to the optical interrogator.

In some embodiments, the console includes the optical interrogator.

In some embodiments, the optical interrogator is a stand-alone unit communicatively coupled to the console.

In some embodiments, the optical-fiber connector module further includes one or more sensors selected from a gyroscope, an accelerometer, and a magnetometer disposed within the housing. The one or more sensors are configured to provide sensor data to the console by way of one or more data wires for determining a reference plane for shape sensing with the optical-fiber stylet.

In some embodiments, the optical-fiber connection module is configured to sit within a fenestration of a surgical drape adjacent a percutaneous insertion site for a catheter.

In some embodiments, the optical-fiber connection module is configured to sit beneath a surgical drape on a patient's chest. The first plug of the medical device is configured for establishing the first optical connection from a sterile field including the medical device to a non-sterile field including the optical-fiber connection module.

Also disclosed herein is a method of an optical-fiber connector module including, in some embodiments, positioning the optical-fiber connector module at a patient's side or on the patient's chest; inserting a first plug of a medical device into a receptacle of the optical-fiber connector module, thereby establishing a first optical connection between the medical device and the optical-fiber connector module; and inserting a second plug of the optical-fiber connector module into a port of a console including an optical interrogator or a standalone optical interrogator, thereby establishing a second optical connection between the optical-fiber connector module and the optical interrogator.

In some embodiments, positioning the optical-fiber connector module at a patient's side includes positioning the optical-fiber connection module within a fenestration of a surgical drape.

In some embodiments, the method further includes disinfecting or sterilizing the optical-fiber connector module before positioning the optical-fiber connection module within the fenestration of the surgical drape.

In some embodiments, positioning the optical-fiber connector module on the patient's chest includes positioning the optical-fiber connection module under a surgical drape or to be under the surgical drape when the surgical drape is placed over the patient.

In some embodiments, inserting the first plug of the medical device into the receptacle of the optical-fiber connector module includes establishing the first optical connection from a sterile field including the medical device to a non-sterile field including the optical-fiber connection module.

In some embodiments, the method further includes conveying input optical signals from the optical interrogator to an optical-fiber stylet of the medical device and reflected optical signals from the optical-fiber stylet to the optical interrogator by way of an optical fiber extending from the receptacle along a cable of the optical-fiber connector module to the second plug.

These and other features of the concepts provided herein will become more apparent to those of skill in the art in view of the accompanying drawings and following description, which describe particular embodiments of such concepts in greater detail.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

Unless defined otherwise, all technical and scientific terms used herein have the same meaning as commonly understood by those of ordinary skill in the art.

As set forth above, there is a need for an optical-fiber connector module that allows for single-use medical devices such as the foregoing PICCs and CVCs to be at least optically connected to non-sterile capital equipment without compromising sterile conditions. Disclosed herein are optical-fiber connector modules, shape-sensing systems including the optical-fiber connector modules, and methods thereof.

For example, an optical-fiber connector module is disclosed including, in some embodiments, a housing, a receptacle disposed in the housing, a cable extending from the housing, and an optical fiber within at least the cable. The receptacle is configured to accept insertion of a first plug for establishing a first optical connection between the optical-fiber connector module and an optical-fiber stylet of a medical device. The cable includes a second plug for establishing a second optical connection between the optical-fiber connector module and an optical interrogator. The optical fiber extends from the receptacle through the cable to the second plug. The optical fiber is configured to convey input optical signals from the optical interrogator to the optical-fiber stylet and reflected optical signals from the optical-fiber stylet to the optical interrogator.

These and other features of the optical-fiber connector modules provided herein will become more apparent with reference to the accompanying drawings and the following description, which provide particular embodiments of the optical-fiber connector modules in greater detail. For context, shape-sensing systems are described first followed by medical devices and optical-fiber connector modules of the shape-sensing systems, as well as methods of the foregoing.

Shape-Sensing Systems

Figure 1:
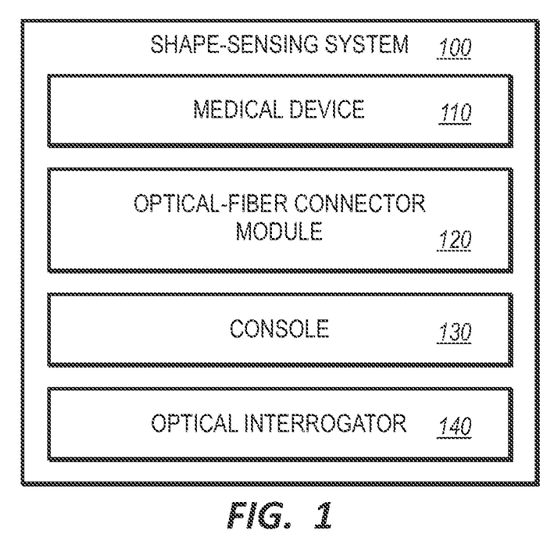
FIG. 1 is a block diagram of a first shape-sensing system in accordance with some embodiments.
Figure 2:
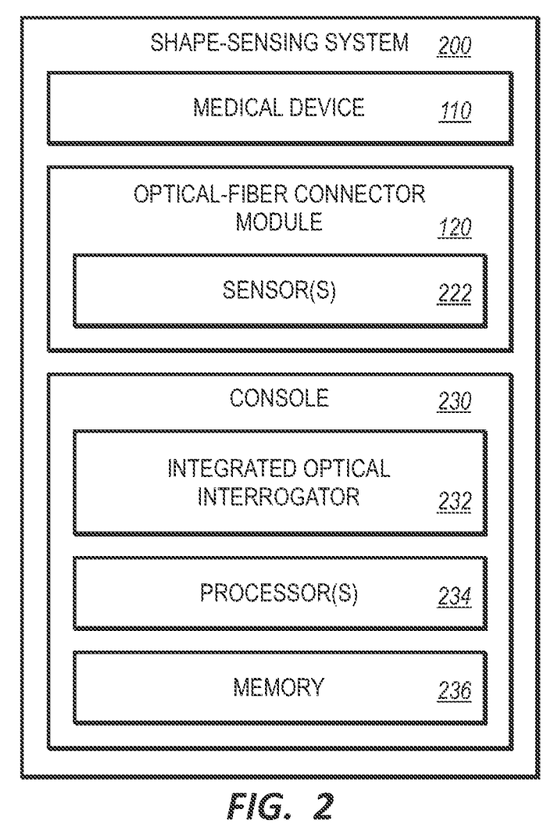
FIG. 2 is a block diagram of a second shape-sensing system in accordance with some embodiments.
Figure 3:
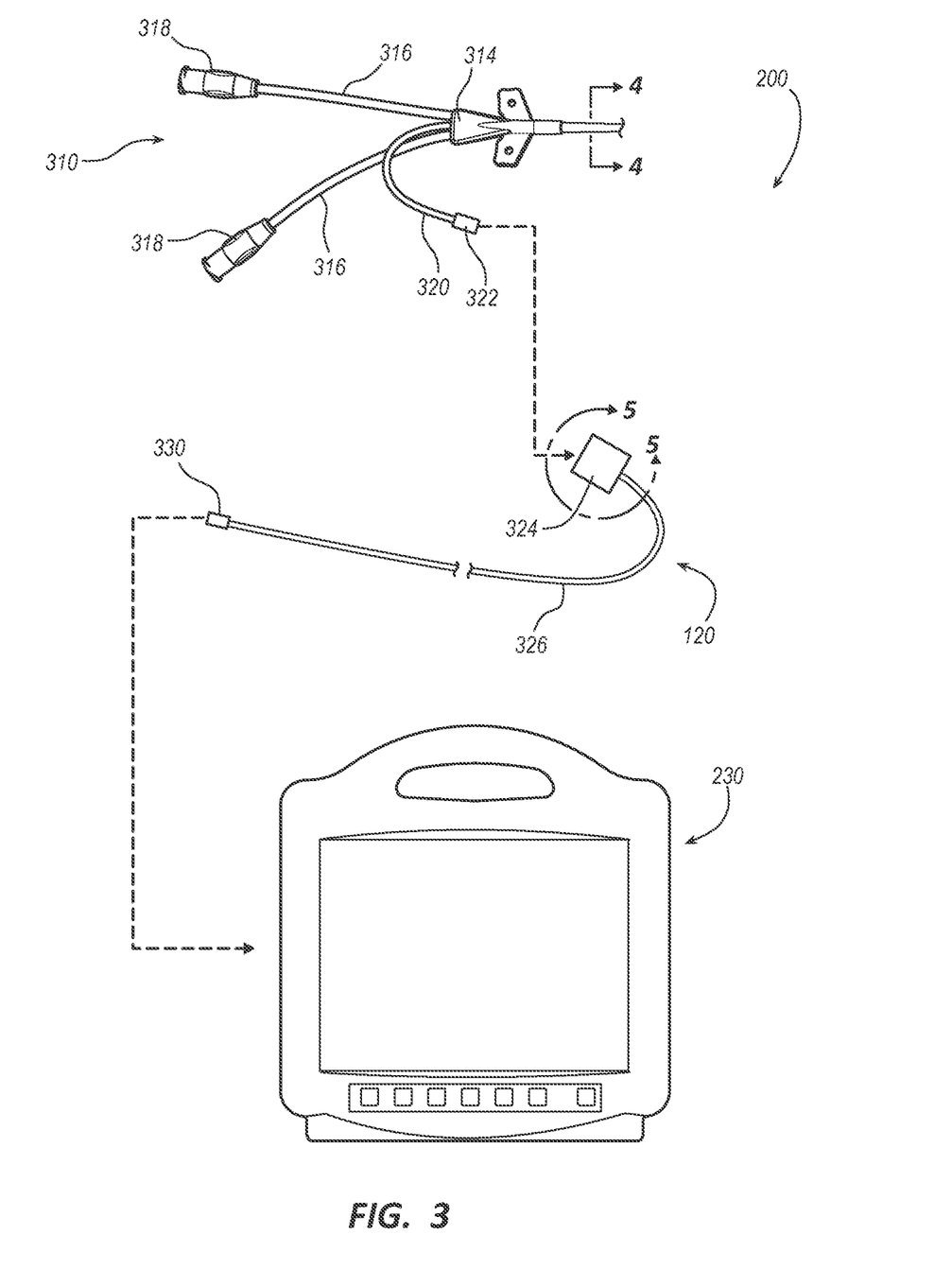
FIG. 3 illustrates the second shape-sensing system in accordance with some embodiments.

FIG. 1 is a block diagram of a first shape-sensing system 100 in accordance with some embodiments. FIG. 2 is a block diagram of a second shape-sensing system 200 in accordance with some embodiments. FIG. 3 illustrates the second shape-sensing system 200 in accordance with some embodiments.

As shown, the shape-sensing system 100 or 200 includes, in some embodiments, a medical device 110, a console 130 or 230, and optical-fiber connector module 120 configured for connecting the medical device 110 to a remainder of the shape-sensing system 100 or 200 such as the console 230.

The medical device 110 includes an integrated optical-fiber stylet having a number of fiber Bragg grating ("FBG") sensors along a length of the optical-fiber stylet for shape sensing with the shape-sensing system 100 or 200. (See integrated optical-fiber stylet 424 in FIG. 4 for an example of the integrated optical-fiber stylet of the medical device 110.)

Certain features of the medical device 110 are set forth in more detail below with respect to particular embodiments of the medical device 110 such as the PICC 310. That said, some features set forth below with respect to one or more embodiments of the medical device 110 are shared among two or more embodiments of the medical device 110. As such, "the medical device 110" is used herein to generically refer to more than one embodiment of the medical device 110 when needed for expository expediency. This is despite certain features having been described with respect to particular embodiments of the medical device 110 such as the PICC 310.

While only shown for the console 230, each console of the consoles 130 and 230 includes memory 236 and one or more processors 234 for algorithmically converting reflected optical signals from the optical-fiber stylet of the medical device 110 into displayable shapes for the medical device 110. The displayable shapes for the medical device 110 can be displayed on an integrated display screen integrated into the console 130 or 230 or a stand-alone monitor coupled to the console 130 or 230.

The shape-sensing system 100 further includes a stand-alone optical interrogator 140 communicatively coupled to the console 130, whereas the shape-sensing system 200 further includes an integrated optical interrogator 232 integrated into the console 230. The optical interrogator 140 or 233 is configured to send input optical signals into the optical-fiber stylet of the medical device 110 by way of the optical-fiber connector module 120 and receive the reflected optical signals from the optical-fiber stylet by way of the optical-fiber connector module 120.

The optical-fiber connector module 120 includes a housing 324, a cable 326 extending from the housing 324, and an optical fiber 528 within at least the cable 326. (For the optical fiber 528, see FIG. 5.) The optical-fiber connector module 120 is configured to establish a first optical connection between the optical-fiber stylet of the medical device 110 and the optical fiber 528 of the optical-fiber connector module 120. The optical-fiber connector module 120 is also configured with a plug 330 at a terminus of the cable 326 to establish a second optical connection between the optical fiber 528 of the optical-fiber connector module 120 and the optical interrogator 140 or 232. The optical fiber 528 of the optical-fiber connector module 120 is configured to convey the input optical signals from the optical interrogator 140 or 232 to the optical-fiber stylet of the medical device 110 and the reflected optical signals from the optical-fiber stylet to the optical interrogator 140 or 232.

The optical-fiber connector module 120 can further include one or more sensors 222 selected from at least a gyroscope, an accelerometer, and a magnetometer disposed within the housing 324. The one or more sensors 222 are configured to provide sensor data to the console 130 or 230 by way of one or more data wires within at least the cable 326 for determining a reference plane for shape sensing with the optical-fiber stylet of the medical device 110.

Certain features of the optical-fiber connector module 120 are set forth in more detail below with respect to particular embodiments of the optical-fiber connector module 120 such as the optical-fiber connector module 620 and 820. That said, some features set forth below with respect to one or more embodiments of the optical-fiber connector module 120 are shared among two or more embodiments of the optical-fiber connector module 120. As such, "the optical-fiber connector module 120" is used herein to generically refer to more than one embodiment of the optical-fiber connector module 120 when needed for expository expediency. This is despite certain features having been described with respect to particular embodiments of the optical-fiber connector module 120 such as the optical-fiber connector modules 620 and 820.

Medical Devices

Figure 4:
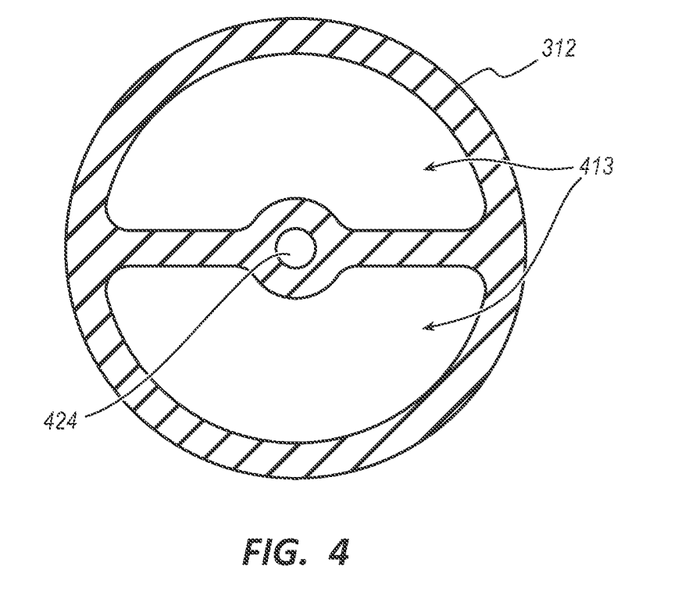
FIG. 4 illustrates a cross-section of a catheter tube of a medical device in accordance with some embodiments.

FIG. 3 also illustrates a PICC 310 as the medical device 110 in accordance with some embodiments. FIG. 4 illustrates a cross-section of a catheter tube 312 of the PICC 310 including an integrated optical-fiber stylet 424 in accordance with some embodiments.

As shown, the PICC 310 includes the catheter tube 312, a bifurcated hub 314, two extension legs 316, and two Luer connectors 318 operably connected in the foregoing order. The catheter tube 312 includes two catheter-tube lumens 413 and the optical-fiber stylet 424 disposed in a longitudinal bead of the catheter tube 312 such as between the two catheter-tube lumens 413, as extruded. Optionally, in a same or different longitudinal bead of the catheter tube 312, the PICC 310 can further include an electrocardiogram ("ECG") stylet. The bifurcated hub 314 has two hub lumens correspondingly fluidly connected to the two catheter-tube lumens 413. Each extension leg of the two extension legs 316 has an extension-leg lumen fluidly connected to a hub lumen of the two hub lumens. The PICC 310 further includes a stylet extension tube 320 extending from the bifurcated hub 314. The stylet extension tube 320 can be a skived portion of the catheter tube 312 including the optical-fiber stylet 424 or the skived portion of the catheter tube 312 disposed in another tube, either of which can terminate in a plug 322 for establishing an optical connection between the optical fiber 528 of the optical-fiber connector module 120 and the optical-fiber stylet 424 of the PICC 310.

While the PICC 310 is provided as a particular embodiment of the medical device 110 of the shape-sensing system 100 or 200, it should be understood that any of a number of medical devices including catheters such as a CVC can include at least an optical-fiber stylet and a stylet extension tube terminating in a plug for establishing an optical connection between the optical-fiber stylet of the medical device and the optical fiber 528 of the optical-fiber connector module 120.

Optical-Fiber Connector Modules

Figure 5:
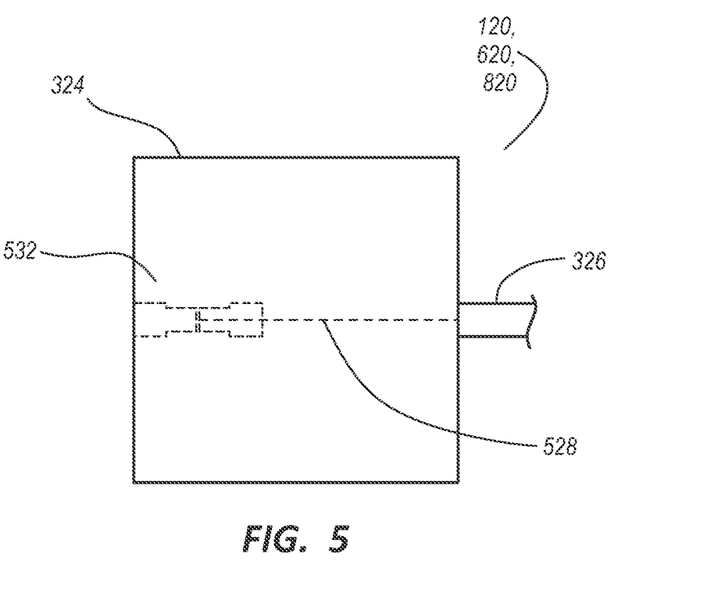
FIG. 5 illustrates a detailed section of an optical-fiber connector module in accordance with some embodiments.
Figure 6:
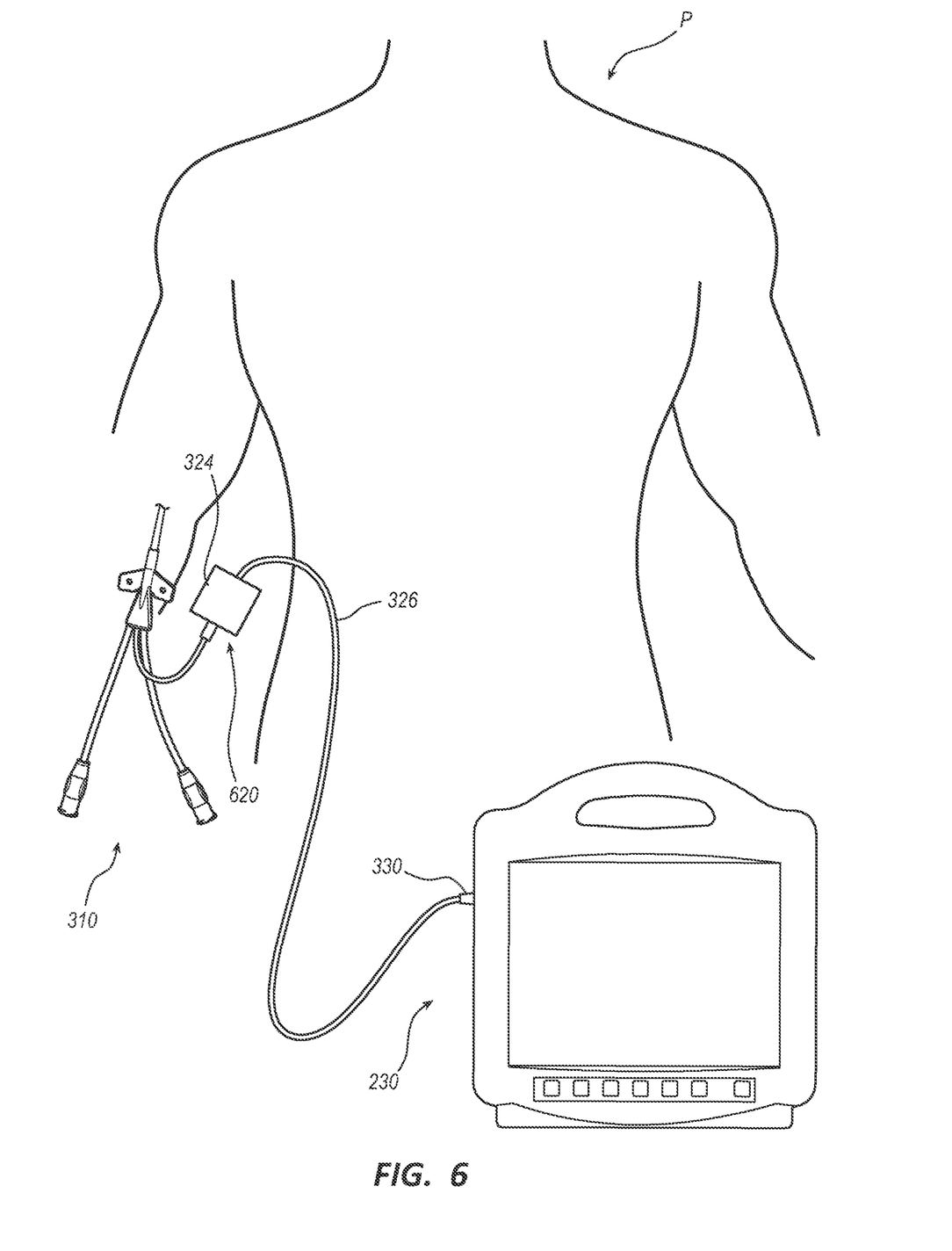
FIG. 6 illustrates the second shape-sensing system with a first optical-fiber connector module in accordance with some embodiments.
Figure 7:
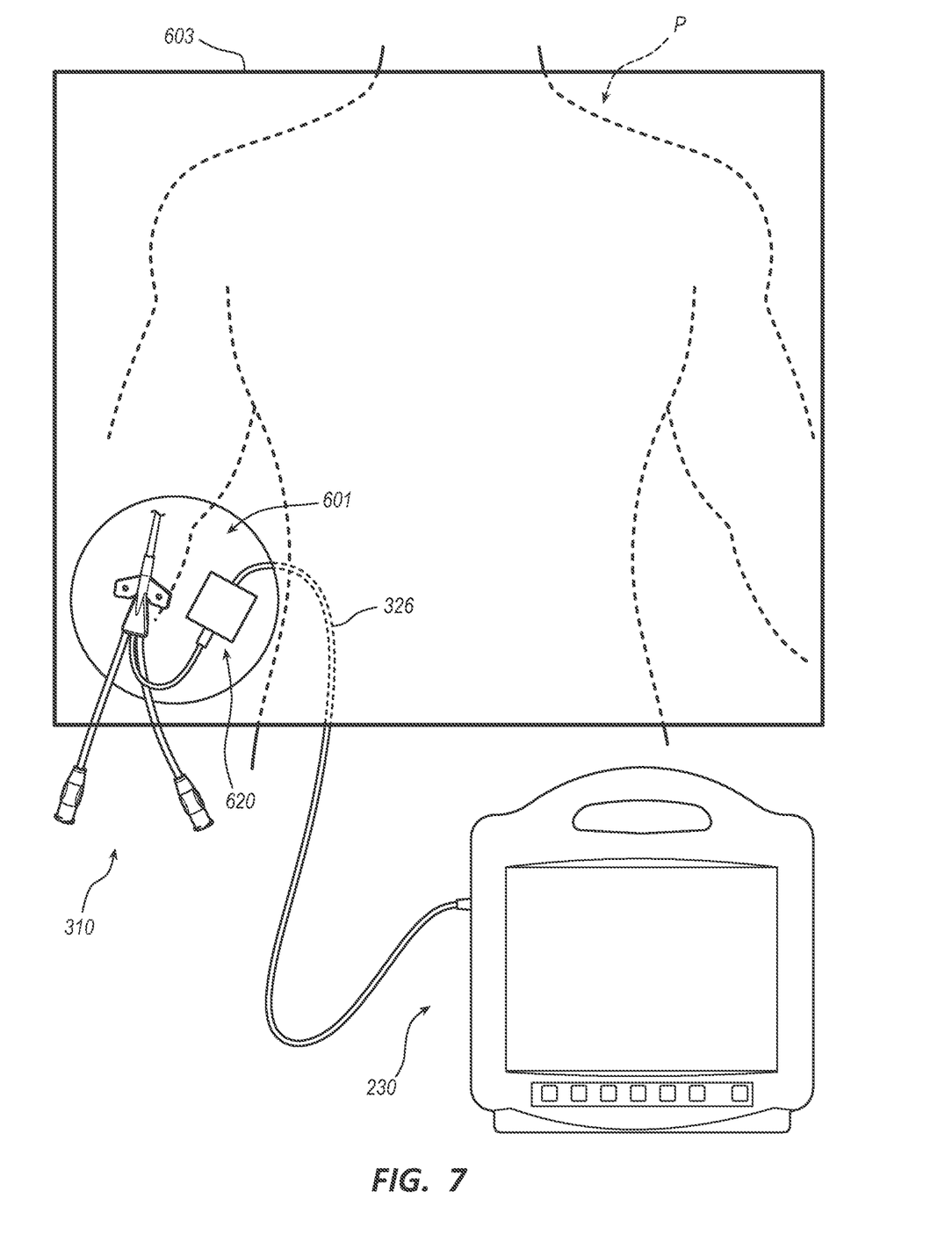
FIG. 7 illustrates the second shape-sensing system with the first optical-fiber connector module within a fenestration of a surgical drape in accordance with some embodiments.
Figure 8:
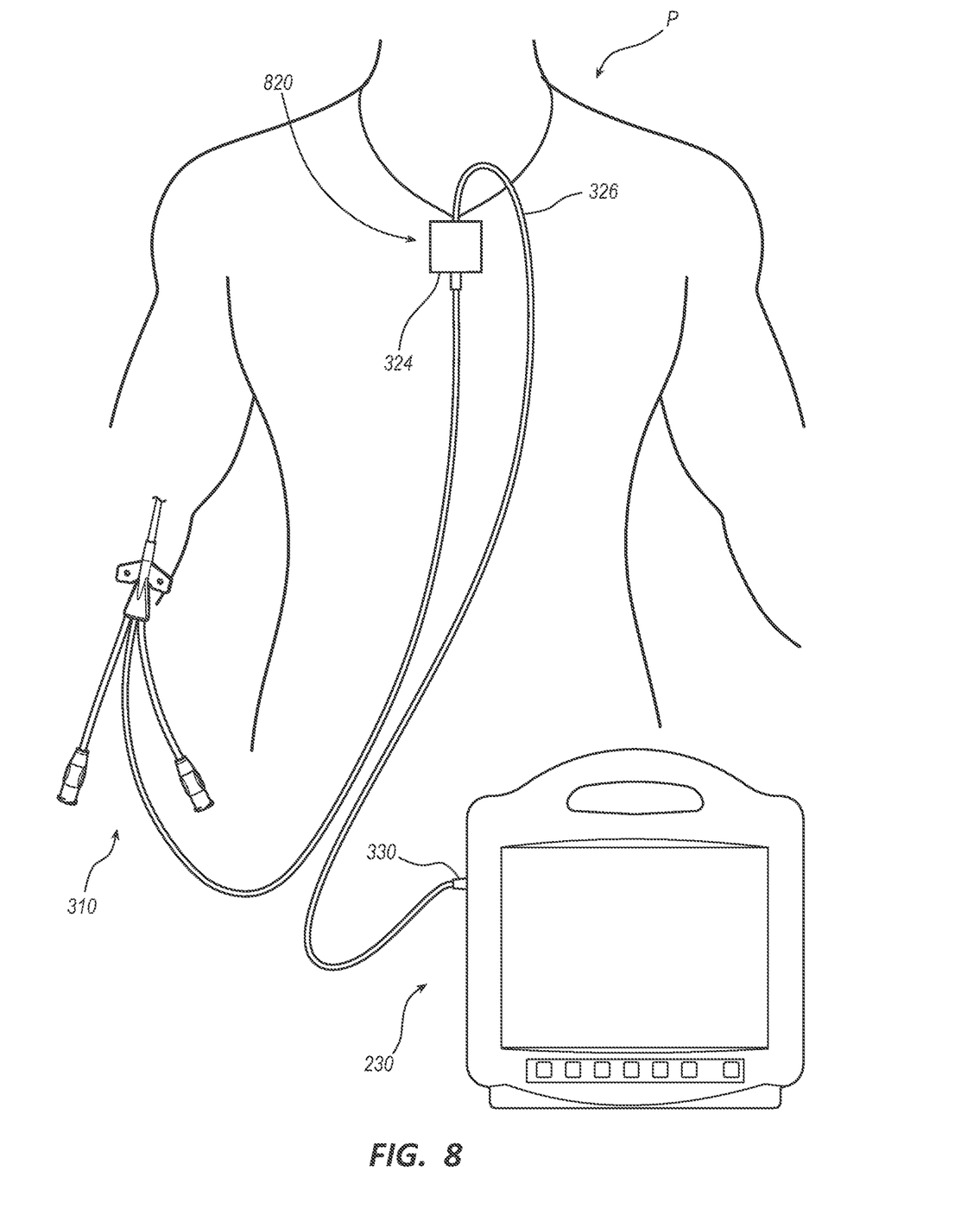
FIG. 8 illustrates the second shape-sensing system with a second optical-fiber connector module in accordance with some embodiments.
Figure 9:
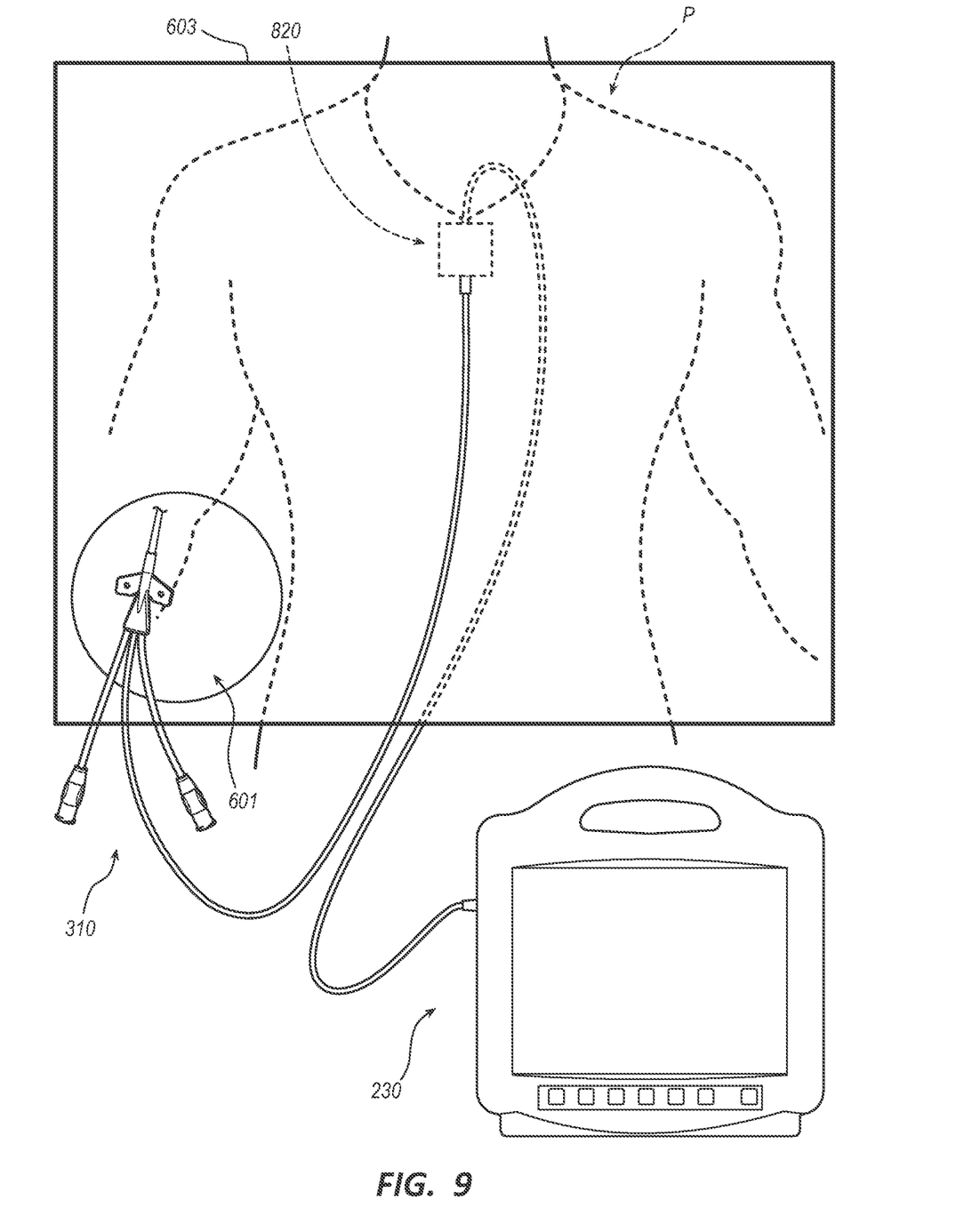
FIG. 9 illustrates the second shape-sensing system with the second optical-fiber connector module beneath a surgical drape in accordance with some embodiments.

FIG. 6 illustrates the second shape-sensing system 200 with a first optical-fiber connector module 620 in accordance with some embodiments. FIG. 7 illustrates the second shape-sensing system 200 with the first optical-fiber connector module 620 within a fenestration 601 of a surgical drape 603 in accordance with some embodiments. FIG. 8 illustrates the second shape-sensing system 200 with a second optical-fiber connector module 820 in accordance with some embodiments. FIG. 9 illustrates the second shape-sensing system 200 with the second optical-fiber connector module 820 beneath the surgical drape 603 in accordance with some embodiments. FIG. 5 illustrates a detailed section of the optical-fiber connector module 120 in accordance with some embodiments thereof such as the first optical-fiber connector module 620 or the second optical-fiber connector module 820.

As shown, the optical-fiber connector module 620 or 820 includes the housing 324, a receptacle 532 disposed in the housing 324, the cable 326 extending from the housing 324, and an optical fiber 528 within at least the cable 326.

The receptacle 532 includes an optical receiver configured to accept insertion of an optical terminal of a plug of the medical device 110 (e.g., the plug 322 of the PICC 310) for establishing an optical connection between the optical-fiber connector module 620 or 820 and the optical-fiber stylet of the medical device 110 (e.g., the optical-fiber stylet 424 of the PICC 310) when the plug is inserted into the receptacle 532.

The cable 326 includes the plug 330 for establishing an optical connection between the optical-fiber connector module 620 or 820 and the optical interrogator 232 of the console 230.

The optical fiber 528 extends from the receptacle 532 through the cable 326 to the plug 330. The optical fiber 528 is configured to convey the input optical signals from the optical interrogator 232 to the optical-fiber stylet of the medical device 110 (e.g., the optical-fiber stylet 424 of the PICC 310) and the reflected optical signals from the optical-fiber stylet to the optical interrogator 232.

As set forth above, the optical-fiber connector module 620 or 820 can further include the one or more sensors 222 selected from the gyroscope, the accelerometer, and the magnetometer disposed within the housing 324. The one or more sensors 222 are configured to provide sensor data for determining a reference plane for shape sensing with the optical-fiber stylet of the medical device 110 (e.g., the optical-fiber stylet 424 of the PICC 310).

While not shown, the optical-fiber connector module 620 or 820 can further include power and data wires extending from the one or more sensors 222 through the cable 326 to the plug 330 or another plug. The power and data wires are configured to respectively convey power to the one or more sensors 122 and data from the one or more sensors 122 to the console 230 when the one or more sensors 122 are present in either the optical-fiber connector module 620 or 820.

The optical-fiber connection module 620 is configured to sit within the fenestration 601 of the surgical drape 603 adjacent a percutaneous insertion site for the medical device 110 (e.g., a catheter such as the PICC 310). As the optical-fiber connection module 620 is configured to sit within the fenestration 601 of the surgical drape 603, the optical-fiber connection module 620 is amenable to disinfection or sterilization. For example, the housing 324 of the optical-fiber connection module 620 can be a non-porous or chemically resistant to oxidants. The optical-fiber connection module 620 can be configured for manual disinfection with a ChloraPrep® product by Becton, Dickinson and Company (Franklin Lakes, N.J.), or the optical-fiber connection module 620 can be configured for automatic high-level disinfection or sterilization with vaporized $H_2O_2$ by way of Trophon® by Nanosonics Inc. (Indianapolis, IN).

In contrast to the optical-fiber connection module 620, the optical-fiber connection module 820 is configured to sit beneath the surgical drape 603 on a chest of a patient P. As such, the optical-fiber connection module 820 need not require a same level of disinfection or sterilization as the optical-fiber connection module 620.

While not shown, the housing 324 the optical-fiber connection module 820 includes a loop extending from the housing 324, a tether point integrated into the housing 324, or a ball-lock-pin receiver integrated into the housing 324 configured for attaching a neck strap to the optical-fiber connector module 820. The loop, the tether point, or the ball-lock-pin receiver enables the optical-fiber connector module 820 to be secured to a neck of the patient P while sitting on the patient's chest. Additionally or alternatively, the housing 324 includes a patient-facing surface (e.g., a back of the optical-fiber connection module 820) configured to be adhered to the patient's chest. The patient-facing surface enables the optical-fiber connector module 820 to be secured to the patient's chest while sitting on the patient's chest whether or not the optical-fiber connection module 820 is also secured to the patient's neck.

Again, the receptacle 532 includes an optical receiver configured to accept insertion of an optical terminal of a plug of the medical device 110 (e.g., the plug 322 of the PICC 310) and form an optical connection when the plug is inserted into the receptacle 532; however, with the optical-fiber connector module 820, the optical connection is formed with the surgical drape 603 between the optical-fiber connector module 820 and the medical device 110. The receptacle 532 and the plug of the medical device 110 enable at least the optical connection from a sterile field (e.g., above the surgical drape 603) including the medical device 110 such as the PICC 310 to a non-sterile field (e.g., beneath the surgical drape 603) including the optical-fiber connection module 820.

Methods

A method of the optical-fiber connector module 620 or 820 includes positioning the optical-fiber connector module 620 at the patient's side or the optical-fiber connector module 820 on the patient's chest; inserting the plug of the medical device 110 (e.g., the plug 322 of the PICC 310) into the receptacle 532 of the optical-fiber connector module 620 or 820, thereby establishing a first optical connection between the medical device 110 and the optical-fiber connector module 620 or 820; and inserting the plug 330 of the optical-fiber connector module 620 or 820 into a port of the console 230 including the integrated optical interrogator 232 or the standalone optical interrogator 140, thereby establishing a second optical connection between the optical-fiber connector module 620 or 820 and the optical interrogator 140 or 232.

Positioning the optical-fiber connector module 620 at the patient's side includes positioning the optical-fiber connection module 620 within the fenestration 601 of the surgical drape 603.

With respect to at least the optical-fiber connector module 620, the method can further include disinfecting or sterilizing the optical-fiber connector module 620 before positioning the optical-fiber connection module 620 within the fenestration 601 of the surgical drape 603.

Positioning the optical-fiber connector module 820 on the patient's chest includes positioning the optical-fiber connection module 820 under the surgical drape 603. Alternatively, positioning the optical-fiber connector module 820 on the patient's chest includes positioning the optical-fiber connection module 820 to be under the surgical drape 603 when the surgical drape 603 is placed over the patient P.

Inserting the plug of the medical device 110 (e.g., the plug 322 of the PICC 310) into the receptacle 532 of the optical-fiber connector module 820 includes establishing the first optical connection from a sterile field including the medical device 110 to a non-sterile field including the optical-fiber connection module 820, thereby breaching the surgical drape 603 without compromising the sterile field.

The method can further include conveying the input optical signals from the optical interrogator 232 to the optical-fiber stylet of the medical device 110 (e.g., the optical-fiber stylet 424 of the PICC 310) and the reflected optical signals from the optical-fiber stylet to the optical interrogator 232 by way of the optical fiber 528 extending from the receptacle 532 along the cable 326 of the optical-fiber connector module 620 or 820 to the plug 330 thereof.

While the foregoing methods are described in reference to the second shape-sensing system 200 including the integrated optical interrogator 232 of the console 230, any of the foregoing methods can alternatively include the first shape-sensing system 100 including the console 130 and the stand-along optical interrogator 140.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An optical-fiber connector module, comprising:
a housing;
a receptacle disposed in the housing, the receptacle configured to accept insertion of a first plug for establishing a first optical connection between the optical-fiber connector module and an optical-fiber stylet of a medical device;
one or more sensors selected from the group consisting of a gyroscope, an accelerometer, and a magnetometer, the one or more sensors disposed within the housing and configured to provide sensor data for determining a reference plane for shape sensing with the optical-fiber stylet;
a cable extending from the housing, the cable including a second plug for establishing a second optical connection between the optical-fiber connector module and an optical interrogator; and
an optical fiber extending from the receptacle through the cable to the second plug, the optical fiber configured to convey input optical signals from the optical interrogator to the optical-fiber stylet and reflected optical signals from the optical-fiber stylet to the optical interrogator,
wherein the optical-fiber connector module is configured to sit on a patient's chest beneath a surgical drape, and
wherein the housing includes a patient-facing surface configured to be adhered to the patient's chest, thereby enabling the optical-fiber connector module to be secured to the patient's chest while sitting on the patient's chest.

2. The optical-fiber connector module of claim 1, further comprising power and data wires extending from the one or more sensors through the cable to the second plug or a third plug, the power and data wires configured to respectively convey power to the one or more sensors and data from the one or more sensors.

3. The optical-fiber connector module of claim 1, wherein the optical-fiber connector module is configured to sit within a fenestration of the surgical drape adjacent a percutaneous insertion site for a catheter.

4. The optical-fiber connector module of claim 3, wherein the optical-fiber connector module is amenable to high-level disinfection or sterilization.

5. The optical-fiber connector module of claim 1, wherein the housing includes at least one of a loop extending from the housing, or a ball-lock-pin receiver integrated into the housing, the at least one of a loop extending from the housing, or a ball-lock-pin receiver integrated into the housing configured for attaching a neck strap to the optical-fiber connector module, thereby enabling the optical-fiber connector module to be secured to a patient's neck while sitting on the patient's chest.

6. The optical-fiber connector module of claim 1, wherein the receptacle includes an optical receiver configured to accept insertion of an optical terminal of the first plug and form the first optical connection when the first plug is inserted into the receptacle with the surgical drape therebetween, thereby enabling the first optical connection to extend from a sterile field to a non-sterile field.

7. A shape-sensing system for medical devices, comprising:
- a medical device including an integrated optical-fiber stylet having a number of fiber Bragg grating ("FBG") sensors along a length of the integrated optical-fiber stylet;
- a console including memory and one or more processors for converting reflected optical signals from the integrated optical-fiber stylet into shapes for the medical device for display;
- an optical-fiber connector module including:
  - a receptacle disposed in a housing, the receptacle configured to accept insertion of a first plug of the medical device for establishing a first optical connection between the optical-fiber connector module and the integrated optical-fiber stylet;
  - one or more sensors selected from the group consisting of a gyroscope, an accelerometer, and a magnetometer, the one or more sensors disposed within the housing and configured to provide sensor data to the console by way of one or more data wires for determining a reference plane for shape sensing with the integrated optical-fiber stylet; and
  - a cable extending from the housing, the cable including a second plug for establishing a second optical connection between the optical-fiber connector module and an optical interrogator; and
- an optical fiber extending from the receptacle through the cable to the second plug, the optical fiber configured to convey input optical signals from the optical interrogator to the integrated optical-fiber stylet and the reflected optical signals from the integrated optical-fiber stylet to the optical interrogator,
- wherein the optical-fiber connector module is configured to sit beneath a surgical drape, and
- wherein the housing includes a patient-facing surface configured to be adhered to a patient's chest, thereby enabling the optical-fiber connector module to be secured to the patient's chest while sitting on the patient's chest.

8. The shape-sensing system of claim 7, wherein the console includes the optical interrogator.

9. The shape-sensing system of claim 7, wherein the optical interrogator is a stand-alone unit communicatively coupled to the console.

10. The shape-sensing system of claim 7, wherein the optical-fiber connector module is configured to sit within a fenestration of the surgical drape adjacent a percutaneous insertion site for a catheter.

11. A method of using an optical-fiber connector module, comprising:
- positioning the optical-fiber connector module at a patient's side or on a patient's chest;
- inserting a first plug of a medical device into a receptacle of the optical-fiber connector module, thereby establishing a first optical connection between the medical device and the optical-fiber connector module; and
- inserting a second plug of the optical-fiber connector module into a port of a console including an optical interrogator or a standalone optical interrogator, thereby establishing a second optical connection between the optical-fiber connector module and the optical interrogator,
- wherein the optical-fiber connector module includes one or more sensors selected from the group consisting of a gyroscope, an accelerometer, and a magnetometer disposed within a housing of the optical-fiber connector module, the one or more sensors configured to provide sensor data for determining a reference plane for shape sensing with an optical-fiber stylet.

12. The method of claim 11, wherein positioning the optical-fiber connector module at the patient's side includes positioning the optical-fiber connector module within a fenestration of a surgical drape.

13. The method of claim 12, further comprising disinfecting or sterilizing the optical-fiber connector module before positioning the optical-fiber connector module within the fenestration of the surgical drape.

14. The method of claim 11, wherein positioning the optical-fiber connector module on the patient's chest includes positioning the optical-fiber connector module under a surgical drape or to be under the surgical drape when the surgical drape is placed over a patient.

15. The method of claim 14, wherein inserting the first plug of the medical device into the receptacle of the optical-fiber connector module includes establishing the first optical connection from a sterile field including the medical device to a non-sterile field including the optical-fiber connector module.

16. The method of claim 11, further comprising conveying input optical signals from the optical interrogator to the optical-fiber stylet of the medical device and reflected optical signals from the optical-fiber stylet to the optical interrogator by way of an optical fiber extending from the receptacle along a cable of the optical-fiber connector module to the second plug.

* * * * *